United States Patent [19]

Smith et al.

[11] Patent Number: 5,691,423
[45] Date of Patent: Nov. 25, 1997

[54] POLYSACCHARIDE-BOUND NITRIC OXIDE-NUCLEOPHILE ADDUCTS

[75] Inventors: Daniel J. Smith, Stow; Debashish Chakravarthy, Garrettsville, both of Ohio; Larry K. Keefer, Bethesda, Md.

[73] Assignee: The United States of America as represented by the Department of Health and Human Services, Washington, D.C.

[21] Appl. No.: 419,424

[22] Filed: Apr. 10, 1995

Related U.S. Application Data

[63] Continuation-in-part of Ser. No. 935,565, Aug. 24, 1992, Pat. No. 5,405,919.
[51] Int. Cl.$^6$ .......................... A61K 31/785; C08B 15/06; C08B 37/00
[52] U.S. Cl. .......................... 525/377; 424/78.17; 424/499; 536/18.7
[58] Field of Search .......................... 525/377; 424/78.17

[56] References Cited

U.S. PATENT DOCUMENTS

| | | |
|---|---|---|
| 3,153,094 | 10/1964 | Reilly. |
| 3,826,832 | 7/1974 | Anderson et al.. |
| 4,265,714 | 5/1981 | Nolan et al.. |
| 4,482,533 | 11/1984 | Keith. |
| 4,638,079 | 1/1987 | Inskip et al.. |
| 4,708,854 | 11/1987 | Grinstead. |
| 4,921,683 | 5/1990 | Bedell. |
| 4,952,289 | 8/1990 | Ciccone et al.. |
| 4,954,526 | 9/1990 | Keefer. |
| 4,985,471 | 1/1991 | Ohta et al.. |
| 5,039,705 | 8/1991 | Keefer et al.. |
| 5,087,631 | 2/1992 | Shaffer et al.. |
| 5,087,671 | 2/1992 | Loeppky et al.. |
| 5,094,815 | 3/1992 | Conboy et al.. |
| 5,155,137 | 10/1992 | Keefer et al. .......................... 514/611 |
| 5,212,204 | 5/1993 | Keefer et al.. |
| 5,234,956 | 8/1993 | Lipton. |
| 5,366,997 | 11/1994 | Keefer et al.. |
| 5,389,675 | 2/1995 | Christodoulou et al.. |
| 5,405,919 | 4/1995 | Keefer et al. .......................... 525/377 |
| 5,482,925 | 1/1996 | Hutsell .......................... 514/11 |

FOREIGN PATENT DOCUMENTS

| | | |
|---|---|---|
| 425154 | 10/1990 | European Pat. Off.. |
| 211789 | 7/1984 | German Dem. Rep.. |
| 2126035 | 12/1971 | Germany. |
| 211789 | 8/1982 | Germany. |
| WO 89/12627 | 6/1989 | WIPO. |
| WO 90/09785 | 9/1990 | WIPO. |
| WO 91/04022 | 4/1991 | WIPO. |
| WO 91/05551 | 5/1991 | WIPO. |
| WO 92/05149 | 4/1992 | WIPO. |
| WO 93/07114 | 4/1993 | WIPO. |
| WO 93/20088 | 10/1993 | WIPO. |
| WO 93/20806 | 10/1993 | WIPO. |
| WO 95/10267 | 4/1995 | WIPO. |
| 96/13164 | 5/1996 | WIPO. |

OTHER PUBLICATIONS

Chakravarthy, Debashish, "Fabrication and Evaluation of Novel Wound Dressings and Related Biomaterials (dextran, microspheres)," *Chemical Abstracts*, 122, No. 26, (1995) Abstract No. 322432.

Mascarenhas, Oscar Carlton, "Epoxy–Based Medical Grade Adhesive Hydrogels and Nitric Oxide Releasing Polymers," *Chemical Abstracts*, 121, No. 18, (1994) Abstract No. 206664.

Smith et al., "Nitric Oxide–Releasing Polymers Containing the [N(o)NO] Group," *Journal of Medical Chemistry*, 39, No. 5, 1148–1156 (1996).

Stamler et al., "S–Nitrosylation of proteins with nitric oxide: Synthesis and characterization of biologically active compounds," *Proc. Natl. Acad. Sci. USA*, 89, 444–448 (1992).

Stamler et al., "Nitric Oxide Circulates in Mammalian Plasma Primarily as an S–Nitroso Adduct of Serum Albumin," *Proc. Natl. Acad. Sci. USA*, 89, 7674–7677 (1992).

Stuehr et al., "Nitric Oxide: A Macrophage Product Responsible for Cytostasis and Respiratory Inhibition in Tumor Target Cells," *J. Exp. Med.*, 169, 1543–1555 (1989).

Thomlinson et al., "The Histological Structure of Some Human Lung Cancers and the Possible Implications for Radiotherapy," *Br. J. Cancer*, IX, 539–549 (1955).

Trissel, "Intravenous Infusion Solutions," *Handbook on Injectable Drugs* (4th ed.), 622–629 (American Society of Hospital Pharmacists, Bethesda, MD) (1986).

von Sonntag, *The Chemical Basis of Radiation Biology*, pp. 31–56 and 295–352 (Taylor & Francis, London) (1987).

Weitz et al., "Zur Kenntnis der stickoxyd–schwefligen Säure (II.Mitteil)," *Berichte d. D. Chem. Gesellschaft*, LXVI, 1718–1727 (1933). (Nitrosylsulfuric acid, *Chemical Abstracts*, 28, 2636.).

WHO Task Group on Environmental Health Criteria for Oxides of Nitrogen, *Environmental Health Criteria 4: Oxides of Nitrogen*, (World Health Organization, Geneva) (1977).

Wiersdorff et al., "N–aryl–N–nitrosohydroxylamine salts," *Chem. Abstracts*, 77, 48034f (1972).

Wilcox et al., "Effect of Cyanide on the Reaction of Nitroprusside with Hemoglobin: Relevance to Cyanide Interference With the Biological Activity of Nitroprusside," *Chem. Res. Toxicol.*, 3, 71–76 (1990).

Wink et al., "DNA Deaminating Ability and Genotoxicity of Nitric Oxide and Its Progenitors," *Science*, 254, 1001–1003 (1991).

(List continued on next page.)

*Primary Examiner*—Peter F. Kulkosky
*Attorney, Agent, or Firm*—Leydig, Voit & Mayer, Ltd.

[57] ABSTRACT

A polymeric composition capable of releasing nitric oxide comprises a polysaccharide including a nitric oxide-releasing $N_2O_2^-$ functional group bound to the polymer; pharmaceutical compositions including the polymeric composition; and methods for treating biological disorders in which dosage with nitric oxide is beneficial. The compositions can be used as and/or incorporated into implants, injectables, condoms, prosthesis coatings, patches, and the like for use in a wide variety of medical applications.

4 Claims, No Drawings

OTHER PUBLICATIONS

Woditsch et al., "Prostacyclin Rather Than Endogenous Nitric Oxide is a Tissue Protective Factor in Myocardial Ischemia," *Am. J. Physiol.*, 263, H1390–H1396 (1992).

Wood et al., "Modification of Energy Metabolism and Radiation Response of A Murine Tumour by Changes in Nitric Oxide Availability," *Biochem. and Biophys. Res. Comm.*, 192, 505–510 (1993).

Zhu et al., "Bactericidal Activity of Peroxynitrite," *Arch. of Biochem. and Biophy.*, 298, 452–457 (1992).

Murayama et al., "Radiosensitization of Hypoxic HeLa S3 Cells in vitro by a New Type of Radiosensitizer: Spermine and Spermidine Amides with Nitro Groups," *Int. J. Radiat. Biol.*, 44, 497–503 (1983).

Myers et al., "Vasorelaxant properties of the endothelium–derived relaxing factor more closely resemble S–nitrosocystein than nitric oxide," *Nature*, 345, 161–163 (1990).

Palmer et al., "Nitric oxide release accounts for the biological activity of endothelium–derived relaxing factor," *Nature*, 327, 324–327 (1987).

Park et al., "Controlled Protein Release from Polyethyleneimine–Coated Poly(L–lactic Acid)/Pluronic Blend Matrices," *Pharmaceut. Res.*, 9, 37–39 (1992).

Phillips et al., "Variation in Sensitizing Efficiency for SR 2508 In Human Cells Dependent on Glutathione Content," *I. J. Radiation Oncology Biol. Phys.*, 12, 1627–1635 (1986).

Phillips et al., "Promise of Radiosensitizers and Radioprotectors in the Treatment of Human Cancer," *Cancer Treatment Reports*, 68, 291–302 (1984).

Powers et al., "A Multicomponent X–Ray Survival Curve for Mouse Lymphosarcoma Cells Irradiated in vivo," *Nature*, 197, 710–711 (1963).

Radi et al., "Peroxynitrite–Induced Membrane Lipid Peroxidation: The Cytotoxic Potential of Superoxide and Nitric Oxide," *Arch. Biochem. and Biophys.*, 288, 481–487 (1991).

Radomski et al., "Endogenous Nitric Oxide Inhibits Human Platelet Adhesion to Vascular Endothelium," *The Lancet*, 1057–1058 (1987).

Rubanyi et al., "Cytoprotective Function of Nitric Oxide: Inactivation of Superoxide Radicals Produced by Human Leukocytes," *Biochem. and Biophys. Res. Comm.*, 181, 1392–1397 (1991).

Russo et al., "The Effects of Cellular Glutathione Elevation on the Oxygen Enhancement Ratio," *Radiation Research*, 103, 232–239 (1985).

Saavedra et al., "Secondary Amine/Nitric Oxide Complex Ions, $R_2N[N](O)NO^-$ O–Functionalized Chemistry," *J. Org. Chem.*, 57, 6134–6138 (1992).

Saran et al., "Reaction of NO With $O_2^-$—. Implications for the Action of Endothelium–Derived Relaxing Factor (EDRF)," *Free Rad. Res. Comm.*, 10, 221–226 (1990).

Siegfried et al., "Beneficial effects of SPM–5185, a cysteine–containing NO donor in myocardial ischemia–reperfusion," *Am. J. Physiol.*, 263, H771–H777 (1992).

Siemann et al., "Characterization of Radiation Resistant Hypoxic Cell Subpopulations In KHT Sarcomas. (ii) Cell Sorting," *Br. J. Cancer*, 58, 296–300 (1988).

Smith et al., "Nitroprusside: A Potpourri of Biologically Reactive Intermediates," in *Advances in Experimental Medicine and Biology*, 283, Biological Reactive Intermediates IV (Witmer et al., eds.), 365–369 (Plenum Press, New York, NY) (1991).

Smith et al., "Complex Contractile Patterns in Canine Colon Produced by Spontaneous Release of Nitric Oxide," *Gastroenterology*, 102 (Part 2), A516 (1992).

Lefer et al., "Pharmacology of the Endothelium in Ischemia–Reperfusion and Circulatory Shock," *Ann. Rev. Pharmacol. Toxicol.*, 33, 71–90 (1993).

Linz et al., "ACE–Inhibition Induces NO–Formation in Cultured Bovine Endothelial Cells and Protects Isolated Ischemic Rat Hearts," *J. Mol. Cell Cardiol.*, 24, 909–919 (1992).

Lipton et al., "A Redox–Based Mechanism for the Neuroprotective and Neurodestructive Effects of Nitric Oxide and Related Nitroso–Compounds," *Nature*, 364, 626–631 (1993).

Longhi et al., "Metal–Containing Compounds of the Anion $(C_2H_5)_2NN_2O_2^-$," *Inorg. Chem.*, 2, 85–88 (1963).

Lutz et al., "Isolation of Trioxodinitrato(II) Complexes of Some First Row Transition Metal Ions," *J.C.S. Chem. Comm.*, 247 (1977).

Maragos et al., "Complexes of •NO with Nucleophiles as Agents for the Controlled Biological Release of Nitric Oxide. Vasorelaxant Effects," *J. Med. Chem.*, 34, 3242–3247 (1991).

Maragos et al., "Nitric Oxide/Nucleophile Complexes Inhibit the in vitro Proliferation of A375 Melanoma Cells via Nitric Oxide Release," *Cancer Res.*, 53 (3), 564–568 (1993).

Marletta et al., "Unraveling the Biological Significance of Nitric Oxide," *BioFactors*, 2, 219–225 (1990).

Marmo et al., "Cardiovascular and Respiratory Effects of Spermidine and Spermine: An Experimental Study," *Biomed. Biochim. Acta*, 43, 509–515 (1984).

Masini et al., "Effect of Nitric Oxide Generators on Ischemia–Reperfusion Injury and Histamine Release in Isolated Perfused Guinea Pig Heart," *Int. Arch. Allergy Appl. Immunol*, 94, 257–258 (1991).

Masini et al., "The Effect of Nitric Oxide Generators on Ischemia Reperfusion Injury and Histamine Release in Isolated Perfused Guinea–Pig Heart," *Agents and Actions*, 33, 53–56 (1991).

Middleton et al., "Further Studies on the Interaction of Nitric Oxide With Transition–Metal Alkyls," *J. Chem. Soc. Dalton*, 1898–1905, (1981).

Minotti et al., "The Requirement for Iron (III) in the Initiation of Lipid Peroxidation by Iron (II) and Hydrogen Peroxide," *J. Biol. Chem.*, 262, 1098–1004 (1987).

Mitchell et al., "Biologically Active Metal–Independent Superoxide Dismutase Mimics," *Biochemistry*, 29, 2802–2807 (1990).

Mitchell et al., "Cellular Glutathione Depletion by Diethyl Maleate or Buthionine Sulfoximine: No Effect of Glutathione Depletion on the Oxygen Enhancement Ratio," *Radiation Research*, 96, 422–428 (1983).

Morikawa et al., "L–Arginine Decreases Infarct Size Caused by Middle Cerebral Arterial Occlusion in SHR," *Am. J. Physiol.*, 263, H1632–H1635 (1992).

Morley et al., "Mechanism of Vascular Relaxation Induced by the Nitric Oxide (NO)/Nucleophile Complexes, a New Class of NO–Based Vasodilators," *J. Cardiovasc. Pharmacol.*, 21, 670–676 (1993).

Ignarro, "Nitric Oxide: A Novel Signal Transduction Mechanism for Transcellular Communication," *Hypertension*, 16, 477–483 (1990).

Imlay et al., "Toxic DNA Damage by Hydrogen Peroxide Through the Fenton Reaction in vivo and in vitro," *Science*, 240, 640–642 (1988).

Ischiropoulos et al., "Peroxynitrite–Mediated Tyrosine Nitration Catalyzed by Superoxide Dismutase," *Arch. Biochem. and Biophys.*, 298, 431–437 (1992).

Jaeschke et al., "Role of Nitric Oxide in the Oxidant Stress During Ischemia/Reperfusion Injury of the Liver," *Life Sciences*, 50, 1797–1804 (1992).

Jones, "Metastable Polymers of the Nitrogen Oxides. 1. Open Chain Nitric Oxide Analogues of Polythlazyl: A MNDO/AM1 Study," *J. Phys. Chem.*, 95, 2588–2595 (1991).

Kanner et al., "Nitric Oxide as an Antioxidant," *Archives of Biochemistry and Biophysics*, 289, 130–136 (1991).

Keefer et al., "Complexes of Nitric Oxide with Nucleophiles as Agents for the Controlled Biological Release of Nitric Oxide," *Biology of Nitric Oxide, 2, Enzymology, Biochemistry, Immunology*, (Moncada et al., eds.), 153–156 (Portland Press, Chapel Hill, NC) (1992).

Kiedrowski et al., "Sodium Nitroprusside Inhibits N–Methyl–D–aspartate–Evoked Calcium Influx via a Nitric Oxide– and cGMP–Independent Mechanism," *Molecular Pharmacology*, 41, 779–784 (1992).

Kruszyna et al., "Red Blood Cells Generate Nitric Oxide from Directly Acting, Nitrogenous Vasodilators," *Toxicol. Appl. Pharmacol.*, 91, 429–438 (1987).

Kubes et al., "Nitric Oxide Modulates Microvascular Permeability," *Am. J. Physiol.*, 262, H611–H615 (1992).

Kubes et al., "Nitric Oxide: An endogenous Modulator of Leukocyte Adhesion," *Proc. Natl. Acad. Sci. USA*, 88, 4651–4655 (1991).

Kubes et al., "Nitric Oxide Protects Against Ischemia/Reperfusion–Induced Mucosal Dysfunction," *Gastroenterology*, 104, A728 (1993).

Kuhn et al., "Endothelium–Dependent Vasodilatation in Human Epicardial Coronary Arteries: Effect of Prolonged Exposure to Glycerol Trinitrate or SIN–1," *J. Cardiovasc. Pharmacol.*, 14 (Suppl. 11), S47–S54 (1989).

Kuznetsov et al., "Photoelectron spectra and electronic structures of 2–alkoxy–1–tert–alkydiazen–1–oxides and 1–alkoxy–3,3–dialkyltriazen–2–oxides," *J. Mol. Struct.*, 263, 329–341 (1991).

Kwon et al., "Inhibition of Tumor Cell Ribonucleotide Reductase by Macrophage–Derived Nitric Oxide," *J. Exp. Med.*, 174 (4) 761–767 (1991).

Lafon–Cazal et al., "NMDA–Dependent Superoxide Production and Neurotoxicity," *Nature*, 364, 535–537 (1993).

Granger, "Role of Xanthine Oxidase and Granulocytes in Ischemia–Reperfusion Injury," *Am. J. Physiol.*, 255, H1269–H1275 (1988).

Hall, "The Oxygen Effect and Reoxygenation," in *Radiobiology for the Radiologist* (4th ed.), 133–164 (J.P. Lippincott Co., Philadelphia) (1994).

Hall et al., "Extreme Hypoxia; Its Effect on the Survival of Mammalian Cells Irradiated at High and Low Dose–Rates," *Br. J. Radiol.*, 39, 302–307 (1966).

Halliwell et al., "Oxygen Toxicity, Oxygen Radicals, Transition Metals and Disease," *Biochem. J.*, 219, 1–14 (1984).

Halliwell et al., "Biologically Relevant Metal Ion–Dependent Hydroxyl Radical Generation," *FEBS*, 307, 108–112 (1992).

Halliwell et al., "Oxygen Free Radicals and Iron in Relation to Biology and Medicine: Some Problems and Concepts," *Arch. Biochem. and Biophys.*, 246, 501–514 (1986).

Hanbauer et al., "Role of Nitric Oxide in NMDA–Evoked Release of [$^3$H]–Dopamine From Striatal Slices," *Neuroreport*, 3, 409–412 (1992).

Hansen et al., "N–Nitrosation of Secondary Amines by Nitric Oxide via the 'Drago Complex'," in *N–Nitroso Compounds: Occurrence and Biological Effects*, IARC Scientific Publications No. 41, 21–29 (International Agency for Research on Cancer, Lyon, France) (1982).

Hibbs et al., "Nitric Oxide: A Cytotoxic Activated Macrophage Effector Molecule," *Biochem. and Biophys. Res. Comm.*, 157, 87–94 (1988).

Holford et al., "Understanding the Dose–Effect Relationship: Clinical Application of Pharmacokinetic–Pharmacodynamic Models," *Clinical Pharmacokinetics*, 6, 429–453 (1981).

Howard–Flanders, "Effect of Nitric Oxide on the Radiosensitivity of Bacteria," *Nature*, 180, 1991–1192 (1957).

Hrabie et al., "New Nitric Oxide–Releasing Zwitterions Derived from Polyamines," *J. Org. Chem.*, 58, 1472–1476 (1993).

Hutcheson et al., "Role of Nitric Oxide in Maintaining Vascular Integrity in Endotoxin–Induced Acute Intestinal Damage in the Rat," *Br. J. Pharmacol.*, 101, 815–820 (1990).

Ignarro et al., "Mechanism of Vascular Smooth Muscle Relaxation by Organic Nitrates, Nitrites, Nitroprusside and Nitric Oxide: Evidence for the Involvement of S–Nitrosothiols as Active Intermediates," *J. Pharmacol. Exp. Ther.*, 218, 739–749 (1981).

Ignarro, "Endothelium–derived nitric oxide: actions and properties," *The FASEB Journal*, 3, 31–36 (1989).

Ignarro, "Biosynthesis and Metabolism of Endothelium–Derived Nitric Oxide," *Ann. Rev. Pharmacol. Toxicol.*, 30, 535–60 (1990).

Ignarro et al., "The Pharmacological and Physiological Role of Cyclic GMP in Vascular Smooth Muscle Relaxation," *Ann. Rev. Pharmacol. Toxicol.*, 25, 171–191 (1985).

DeGraff et al., "Evaluation of Nitroimidazole Hypoxic Cell Radiosensitizers in a Human Tumor Cell Line High in Intracellular Glutathione," *I. J. Radiation Oncology Biol. Phys.*, 16, 1021–1024 (1989).

DeLuca et al., "Parenteral Drug–Delivery Systems," in *Pharmaceutics and Pharmacy Practice* (Banker et al., eds.), 238–250 (J.B. Lippincott Co., Philadelphia, PA) (1982).

Drago et al., "The Reaction of Nitrogen(II) Oxide with Various Primary and Secondary Amines," *J. Am. Chem. Soc.*, 83, 1819–1822 (1961).

Drago, "Reactions of Nitrogen(II) Oxide," in *Free Radicals in Organic Chemistry*, Advances in Chemistry Series No. 36, 143–149 (American Chemical Society, Washington, DC) (1962).

Fast et al., "Nitric Oxide Production by Tumor Targets in Response to TNF: Paradoxical Correlation With Susceptibility to TNF–Mediated Cytotoxicity Without Direct Involvement in the Cytotoxic Mechanism," *J. Leukocyte Biol.*, 52, 255–261 (1992).

Feelisch et al., "On the Mechanism of NO Release from Sydnonimines," *J. Cardiovasc. Pharmacol.*, 14, S13–S22 (1989).

Feelisch, "The Biochemical Pathways of Nitric Oxide Formation from Nitrovasodilators: Appropriate Choice of Exogenous NO Donors and Aspects of Preparation and Handling of Aqueous NO Solutions," *J. Cardiovasc. Pharmacol.*, 17, S25–S33 (1991).

Feldman et al., "The surprising life of nitric oxide," *Chemical & Engineering News*, 71, 26–38 (1993).

Filep et al., "Nitric Oxide Modulates Vascular Permeability in the Rat Coronary Circulation," *Br. J. Pharmacol.*, 108, 323–326 (1993).

Fujitsuka et al., "Nitrosohydroxylamines,"*Chem. Abstracts*, 82, 31108P (1975).

Furchgott, "The Role of Endothelium in the Responses of Vascular Smooth Muscle to Drugs," *Ann. Rev. Pharmacol. Toxicol.*, 24, 175–97 (1984).

Gambassi et al., "Ischemia–Reperfusion Injury and Histamine Release in Isolated Perfused Guinea–Pig Heart: Effects of Nitric Oxide Generators," *Pharmacological Research*, 25, 11–12 (1992).

Garg et al., "Nitric Oxide–Generating Vasodilators Inhibit Mitogenesis and Proliferation of Balb/C3T3 Fibroblasts By A Cylic GMP–Independent Mechanism," *Biochem. and Biophys. Res. Comm.*, 171, 474–479 (1990).

Gatenby et al., "Oxygen Distribution in Squamous Cell Carcinoma Metastases and its Relationship to Outcome of Radiation Therapy," *I. J. Radiation Oncology Biol. Phys.*, 14, 831–838 (1988).

Gehlen et al., "Über Reaktionen und Eigenschaften des Stickoxyds und seiner Verbindungen (II.Mitteil): Zur Kenntnis der Salze der Stickoxyd–schwefligen Säure," *Berichte d. D. Chem. Gesellschaft*, LXV, 1130–1140 (1932). (Reactions and properties of nitric oxide and its compounds. II. The salts of the nitric oxide compound of sulfurous acid, *Chemical Abstracts*, 26, 4764–65.).

Gelvan et al., "Cardiac Reperfusion Damage Prevented by a Nitroxide Free Radical," *Proc. Natl. Acad. Sci. USA*, 88, 4680–4684 (1991).

Adams et al., "Electron–Affinic Sensitization," *Radiation Research*, 67, 9–20 (1976).

Alston et al., "Generation of Nitric Oxide by Enzymatic Oxidation of N–Hydroxy–N–Nitrosamines," *J. Biol. Chem.*, 260 (7), 4069–4074 (1985).

Ames et al., "Uric Acid Provides An Antioxidant Defense in Humans Against Oxidant–And Radical–Caused Aging and Cancer: A Hypothesis," *Proc. Natl. Acad. Sci. USA*, 78, 6858–6862 (1981).

Andrade et al., "Inhibitors of Nitric Oxide Synthase Selectively Reduce Flow in Tumour–Associated Neovasculature," *Br. J. Pharmacol.*, 107, 1092–1095 (1992).

Andrews et al., "Protection Against Gastric Reperfusion Injury by Nitric Oxide: Role of Polymorhophonuclear Leukocytes," *Gastroenterology*, 104, A33 (1993).

Aoki et al., "Beneficial Effects of Two Forms of NO Administration in Feline Splanchnic Artery Occlusion Shock," *Am. J. Physiol.*, 258, G275–G281 (1990).

Artysbasheva et al., "Synthesis of 1–Alkoxy–3,3–Dialkyltriazene 2–Oxides from Alkoxyamines and Nitrosoamines," translated from *Zhurnal Organicheskoi Khimii* (J. Organic Chemistry–U.S.S.R.), 28, (6) 1168–1173 (1987).

Beckman et al., "Apparent Hydroxyl Radical Production by Peroxynitrite: Implications for Endothelial Injury From Nitric Oxide and Superoxide," *Proc. Natl. Acad. Sci. USA*, 87, 1620–1624 (1990).

Beckman, "The Double–Edged Role of Nitric Oxide in Brain Function and Superoxide–Mediated Injury," *J. Developmental Physiol.*, 15, 53–59 (1991).

Beckman, "Ischaemic Injury Mediator," *Nature*, 345, 27–28 (1990).

Bedford et al., "Threshold Hypoxia: Its Effect on the Survival of Mammalian Cells Irradiated at High and Low Dose–Rates," *Br. J. Radiol.*, 39, 896–900 (1966).

Bohn et al., "Oxygen and Oxidation Promote the Release of Nitric Oxide from Sydnonimines," *J. Cardiovasc. Pharmacol.*, 14, S6–S12 (1989).

Bonakdar et al., "Continuous–Flow Performance of Carbon Electrodes Modified With Immobilized Fe(II)/Fe(III) Centers," *Calanta*, 36, 219–225 (1989).

Coleman et al., "Phase I Trial of the Hypoxic Cell Radiosensitizer SR–2508: The Results of the Five to Six Week Drug Schedule," *Int. J. Radiat. Oncol. Biol. Phys.*, 12, 1105–1108 (1986).

Dawson et al., "Nitric Oxide Synthase and Neuronal NADPH Diaphorase Are Identical in Brain and Peripheral Tissues," *Proc. Natl. Acad. Sci. USA*, 88, 7797–7801 (1991).

DeFeudis, "Endothelium–Dependent Vasorelaxation–A New Basis for Developing Cardiovascular Drugs," *Drugs of Today*, 24 (2), 103–115 (1988).

POLYSACCHARIDE-BOUND NITRIC OXIDE-NUCLEOPHILE ADDUCTS

This application is a continuation in part of U.S. patent application Ser. No. 07/935,565, filed Aug. 24, 1992, now U.S. Pat. No. 5,405,919, the entire disclosure of which is hereby incorporated by reference.

TECHNICAL FIELD OF THE INVENTION

The present invention relates to compositions comprising a nitric oxide/nucleophile adduct capable of releasing nitric oxide. In particular, the present invention relates to compositions comprising nitric oxide/nucleophile adducts which are bound to a polysaccharide and which release nitric oxide in a physiological environment, pharmaceutical compositions comprising such nitric oxide/nucleophile adduct compositions, and methods of using same to treat a biological disorder for which the administration of nitric oxide is indicated.

BACKGROUND OF THE INVENTION

Nitric oxide (NO) has recently been implicated in a variety of bioregulatory processes, including normal physiological control of blood pressure, macrophage-induced cytostasis and cytotoxicity, and neurotransmission (Moncada et al., "Nitric Oxide from L-Arginine: A Bioregulatory System," *Excerpta Medica*, International Congress Series 897 (Elsevier Science Publishers B. V.: Amsterdam, 1990); Marletta et al., "Unraveling the Biological Significance of Nitric Oxide," *Biofactors*, 2, 219–225 (1990); Ignarro, "Nitric Oxide. A Novel Signal Transduction Mechanism for Transcellular Communication," *Hypertension (Dallas)*, 16, 477–483 (1990)). A number of compounds have been developed which are capable of delivering nitric oxide, including compounds which release nitric oxide upon being metabolized and compounds which release nitric oxide spontaneously in aqueous solution.

Those compounds which release nitric oxide upon being metabolized include the widely used nitrovasodilators glyceryl trinitrate and sodium nitroprusside (Ignarro et al., *J. Pharmacol. Exp. Ther.*, 218, 739–749 (1981); Ignarro, *Annu. Rev. Pharmacol. Toxicol.*, 30, 535–560 (1990); Kruszyna et al., *Toxicol. Appl. Pharmacol.*, 91, 429–438 (1987); Wilcox et al., *Chem. Res. Toxicol.*, 3, 71–76 (1990). Another compound, S-nitroso-N-acetylpenicillamine, has been reported to release nitric oxide in solution and to be effective at inhibiting DNA synthesis (Garg et al., *Biochem. and Biophys. Res. Comm.*, 171, 474–479 (1990)).

Numerous nitric oxide-nucleophile complexes have been described, e.g., Drago, *ACS Adv. Chem. Ser.*, Vol. 36, p. 143–149 (1962). See also Longhi and Drago, *Inorg. Chem.* 2 85, (1963). Some of these complexes are known to evolve nitric oxide on heating or hydrolysis, e.g., Maragos et al., *J. Med. Chem.* 34, 3242–3247, 1991.

The cytostatic effect of nitric oxide solutions on tumor cells in vitro has been demonstrated. In particular, it has been shown that solutions of nitric oxide inhibit DNA synthesis and mitochondrial respiration of tumor cells in vitro (Hibbs et al., *Biochem. and Biophys. Res. Comm.*, 157, 87–94 (1988); Stuehr et al., *J. Exp. Med.*, 169, 1543–1555 (1989)).

Endothelium-derived relaxing factor (EDRF) is a labile humoral agent which is part of a cascade of interacting agents involved in the relaxation of vascular smooth muscle. EDRF is thus important in the control of vascular resistance to blood flow and in the control of blood pressure. Some vasodilators act by causing EDRF to be released from endothelial cells. (See Furchgott, *Ann. Rev. Pharmacol. Toxicol.* 24, 175–197, 1984.) In 1987, Palmer et al., presented evidence that EDRF is identical to the simple molecule, nitric oxide, NO (Nature 317, 524–526, 1987), though more recently, that conclusion has been challenged (Myers et al., Nature, 345, 161–163, 1990).

Nitric oxide in its pure form, however, is a highly reactive gas having limited solubility in aqueous media (WHO Task Group on Environmental Health Criteria for Oxides of Nitrogen, *Oxides of Nitrogen*, Environmental Health Criteria 4 (World Health Organization: Geneva, 1977)). Nitric oxide, therefore, is difficult to introduce reliably into most biological systems without premature decomposition.

The difficulty in administering nitric oxide can be overcome in some cases by administering nitric oxide pharmacologically in prodrug form. The compounds glyceryl trinitrate and sodium nitroprusside are relatively stable but release nitric oxide only on redox activation (Ignarro et al., *J. Pharmacol. Exp. Ther.*, 218, 739–749 (1981); Ignarro, *Annu. Rev. Pharmacol. Toxicol.*, 30, 535–560 (1990); Kruszyna et al., *Toxicol. Appl. Pharmacol.*, 91, 429–438 (1987); Wilcox et al., *Chem. Res. Toxicol.*, 3, 71–76 (1990)). While this feature may be an advantage in some applications, it can also be a significant liability, as in the development of tolerance to glyceryl trinitrate via the exhaustion of the relevant enzyme/cofactor system (Ignarro et al., *Annu. Rev. Pharmacol. Toxicol.*, 25, 171–191 (1985); Kuhn et al., *J. Cardiovasc. Pharmacol.*, 14 (Suppl. 11), S47–S54 (1989)) and toxicity from metabolically produced cyanide during prolonged administration of nitroprusside (Smith et al., "A Potpourri of Biologically Reactive Intermediates" in *Biological Reactive Intermediates IV. Molecular and Cellular Effects and Their Impact on Human Health* (Witmer et al., eds.), Advances in Experimental Medicine and Biology Volume 283 (Plenum Press: New York, 1991), pp. 365–369).

Evidence that nitric oxide is released from the endothelial cells and is responsible for the relaxation of the vascular smooth muscle, and hence the control of blood pressure, has resulted in the development of artificial agents that can deliver nitric oxide in vivo. A very important class of such agents is the nitric oxide-nucleophile complexes. Recently, a method for treating cardiovascular disorders in a mammal with certain nitric oxide-nucleophile complexes has been disclosed, e.g. in U.S. Pat. No. 4,954,526. These compounds contain the anionic $N_2O_2^-$ group or derivatives thereof. See also, Maragos et al., J. Med. Chem. 34, 3242–3247, 1991. Many of these compounds have proven especially promising pharmacologically because, unlike nitrovasodilators such as nitroprusside and nitroglycerin, they release nitric oxide without first having to be metabolized. The only other series of drugs currently known to be capable of releasing nitric oxide purely spontaneously is the S-nitrosothiols series, compounds of structure R—S—NO (Stamler et al., Proc. Natl. Acad. Sci. U.S.A. 89, 444–448, 1992); however, the R—S—NO→NO reaction can be kinetically complicated and difficult to control (Morley et al., *J. Cardiovasc. Pharmacol.*, 21, 670–676 (1993)), and extensive redox activation (McAninly et al., *J. Chem. Soc., Chem. Comm.*, 1758–1759 (1993)) and Metalbolism Kowaluk et al., *J. Pharmacol. Exp. Ther.*, 225, 1256–1264 (1990)) have been documented for these compounds. Moreover, the oxidation state of nitrogen in the S-nitrosothiols is +3, rather than the +2 of nitric oxide. While variation in the R group of the R—S—N═O compounds provides a means of altering their chemical, and hence pharmacological, properties, the NONOate series is especially versatile in this respect. NONOates having reproducible half-lives ranging from 2 seconds to 20 hours have been prepared. They can be O-alkylated to provide either spontaneous NO-generators with half-lives of up to a week or more or prodrugs that cannot release NO at all until the oxygen substituent is removed metabolically. The NONOate function can be coordinated via the two oxygen atoms to metal centers; it can be attached to peptides; and it can be bound in solid polymeric matrices to provide a point source of NO. By providing such a wide variety of NO release rates, physical forms, and potential strategies for targeting NO delivery to specific sites in the body, the NONOates constitute a most advantageous series of compounds on which to base NO donor drug development efforts.

Nitric oxide/nucleophile complexes (NONOates) which release nitric oxide in aqueous solution are also disclosed in U.S. Pat. Nos. 4,954,526, 5,039,705, 5,212,204, 5,155,137, 5,208,233, 5,250,550, 5,366,997, and 5,389,675 (see also Maragos et al., *J. Med. Chem.*, 34, 3242–3247 (1991)).

Despite the promise of the monomeric nitric oxide/ nucleophile adducts that have been investigated, their pharmacological application has been limited by their tendency to distribute evenly throughout the medium. Such even distribution is a great advantage in many research applications, but tends to compromise their selectivity of action. Another limitation to the application of some of these nitric oxide/nucleophile adducts is their propensity for relatively rapid release of nitric oxide which may necessitate frequent dosing to achieve a prolonged biological effect. Thus there remains a need for nitric oxide-releasing compositions which are capable of concentrating the effect of the nitric oxide release to a situs of application and for which nitric oxide release may be controlled for effective dosing.

It is therefore a principal object of the present invention to provide a composition which includes a nitric oxide/ nucleophile adduct whose action can be localized to enhance the selectivity of nitric oxide release. Another object of the invention is to provide a composition which includes a nitric oxide/nucleophile adduct whose release of nitric oxide can be controlled to effect efficient dosing for a prolonged biological effect. A further object of the present invention is to provide compositions including nitric oxide/nucleophile adducts capable of releasing nitric oxide wherein the nitric oxide/nucleophile adduct is associated with a polymer. A more specific object of the present invention is to provide polysaccharide compositions including nitric oxide/ nucleophile adducts capable of releasing nitric oxide in the body and which are readily eliminated from the body after the release of NO. These and other objects and advantages of the present invention, as well as additional inventive features, will be apparent from the description of the invention provided herein.

BRIEF SUMMARY OF THE INVENTION

The present invention provides a composition capable of releasing nitric oxide which includes a nitric oxide-releasing $N_2O_2^-$ functional group bound to a polymer, specifically a polysaccharide. By "bound to a polymer," it is meant that the $N_2O_2^-$ functional group is associated with, part of, incorporated with or contained within the polymer matrix physically or chemically. Physical association or bonding of the $N_2O_2^-$ functional group to the polymer may be achieved by coprecipitation of the polymer with a nitric oxide/ nucleophile complex as well as by covalent bonding of the $N_2O_2^-$ group to the polymer. Chemical bonding of the $N_2O_2^-$ functional group to the polymer may be by, for example, covalent bonding of the nucleophile moiety of the nitric oxide/nucleophile adduct to the polymer such that the nucleophile residue to which the $N_2O_2^-$ group is attached forms part of the polymer itself, i.e., is in the polymer backbone or is attached to pendant groups on the polymer backbone. The manner in which the nitric oxide-releasing $N_2O_2^-$ functional group is associated, part of, or incorporated with or contained within, i.e., "bound," to the polymer is inconsequential to the present invention and all means of association, incorporation and bonding are contemplated herein.

The present invention also provides a pharmaceutical composition which includes a pharmaceutically acceptable carrier and a polymer, specifically a polysaccharide, having a nitric oxide-releasing $N_2O_2^-$ functional group bound to said polymer. The polymer-bound nitric oxide-releasing $N_2O_2^-$ functional group compositions of the present invention may themselves function as a pharmaceutical composition, as, for example, when the polymer-bound composition is in the form of an implant, stent, patch, or the like.

The invention further provides a method of treating biological disorders in which dosage with nitric oxide would be beneficial which comprises administering a composition comprising a polymer, specifically a polysaccharide, and a nitric oxide-releasing $N_2O_2^-$ functional group bound to said polymer in an amount sufficient to release a therapeutically effective amount of nitric oxide.

DETAILED DESCRIPTION OF THE PREFERRED EMBODIMENTS

The present invention is predicated on the discovery that useful pharmacological agents can be provided by incorporating nitric oxide-releasing $N_2O_2^-$ functional groups into a polymeric matrix, specifically a polysaccharide. Accordingly, the $N_2O_2^-$ functional group is "bound to the polymer" as that term has been defined herein. It has been discovered that incorporation of the $N_2O_2^-$ functional group into a polymeric matrix provides a polymer-bound nitric oxide/nucleophile adduct composition that can be applied with specificity to a biological site of interest. Site specific application of the polymer-bound adduct composition enhances the selectivity of action of the nitric oxide releasing $N_2O_2^-$ functional group. If $N_2O_2^-$ functional groups attached to the polymer are necessarily localized, then the effect of their nitric oxide release will be concentrated in the tissues with which they are in contact. If the polymer is soluble, selectivity of action can still be arranged, for example, by attachment to or derivatization of an antibody specific to the target tissue. Similarly, attachment of $N_2O_2^-$ containing polysaccharides to small peptides that mimic the recognition sequences of ligands for important receptors provides localized concentrated effect of nitric oxide release, as would attachment to oligonucleotides capable of site-specific interactions with target sequences in a nucleic acid.

Additionally, incorporation of the $N_2O_2^-$ functional group into a polymeric matrix can reduce the propensity of the nitric oxide/nucleophile adduct for the relatively rapid release of nitric oxide. This prolongs the release of nitric oxide by the $N_2O_2^-$ functional group, and allows for efficient dosing to achieve a desired biological effect so the frequency of dosing can be reduced.

While not being bound to any particular theory, it is believed that longevity of nitric oxide release in the polymer-bound nitric oxide/nucleophile adduct compositions of the present invention is to be attributed both to the physical structure of the composition and to electrostatic effects. Thus, it is believed that if the polymer is an insoluble solid, $N_2O_2^-$ groups near the surface of the particle should be available for rapid release while those that are more deeply imbedded are sterically shielded, requiring more time and/or energy for the nitric oxide to work its way into the medium. Unexpectedly, it has been found that increasing positive charge in the vicinity of an $N_2O_2^-$ functional group also tends to increase the halflife of nitric oxide generation. The mechanism of this rate retardation may be attributable simply to repulsive electrostatic interactions, i.e., increasing the number of $H^+$-repelling positive charges in the vicinity of the $N_2O_2^-$ groups inhibits attack of positively charged $H^+$ ions on the $N_2O_2^-$ functional group and slows the rate of its $H^+$-catalyzed decomposition. For example, by attaching amino groups to the polymeric support that are capable of forming the nitric oxide-releasing $N_2O_2^-$ functional group on reaction with nitric oxide, partially converted structures can be produced on less-than-exhaustive treatment with nitric oxide that after exposure to water contain a large number of positively charged ammonium centers surrounding the $N_2O_2^-$ group that electrostatically inhibit the approach of $H^+$ ions capable of initiating nitric oxide loss from the nitric oxide releasing $N_2O_2^-$ functional group.

The nitric oxide-releasing $N_2O_2^-$ functional groups that are bound to the polymer generally are capable of releasing nitric oxide in an aqueous environment spontaneously upon contacting an aqueous environment, i.e., they do not require activation through a redox reaction or electron transfer such as is required for glyceryl trinitrate and sodium nitroprusside. Some of the nitric oxide/nucleophile complexes useful in the context of the present invention do require activation by particular means, but only as necessary to free the nitric oxide releasing X-[N(O)NO]$^-$ group in the vicinity of the particular cells of interest. As an example, covalent attachment of a protecting group to the anionic [N(O)NO]$^-$ function provides a means of postponing nitric oxide release until the molecule reaches an organ capable of metabolically removing the protecting group. By choosing a protecting group that is selectively cleaved by enzymes specific to a tumor, biological disorder, cell, or tissue of interest, for example, the action of the nitric oxide/nucleophile complex can be targeted to maximize the desired effect. While the polymer-bound, i.e., polysaccharide-bound, nitric oxide-releasing compositions of the present invention are capable of releasing nitric oxide in an aqueous solution, such a compound preferably releases nitric oxide under physiological conditions.

The nitric oxide releasing $N_2O_2^-$ functional group is preferably a nitric oxide/nucleophile adduct, e.g., a complex of nitric oxide and a nucleophile, most preferably a nitric oxide/nucleophile complex which contains the moiety [N(O)NO]-X or X-[N(O)NO], where X is any suitable nucleophile residue and may be an organic or inorganic moiety. The nucleophile residue is preferably that of a primary amine (e.g., X=(CH$_3$)$_2$CHNH, as in (CH$_3$)$_2$CHNH [N(O)NO]Na), a secondary amine (e.g., X=(CH$_3$CH$_2$)$_2$N, as in (CH$_3$CH$_2$)$_2$N[N(O)NO]Na), a polyamine (e.g., X=spermine, as in the zwitterion H$_2$N(CH$_2$)$_3$NH$_2^+$(CH$_2$)$_4$N [N(O)NO]$^-$ (CH$_2$)$_3$NH$_2$, or X=3-(n-propylamino) propylamine, as in the zwitterion CH$_3$CH$_2$CH$_2$N[N(O)NO]$^-$ CH$_2$CH$_2$CH$_2$NH$_3^+$), or oxide (i.e., X=O$^-$, as in NaO[N(O) NO]Na), or a derivative thereof. Such nitric oxide/nucleophile complexes are stable solids and are capable of delivering nitric oxide in a biologically usable form at a predictable rate.

The nucleophile residue is preferably not an entity such as that of sulfite (e.g., X=SO$_3^-$, as in NH$_4$O$_3$S[N(O)NO]NH$_4$) even though the complex is a stable compound, since it is capable of releasing nitric oxide in an aqueous environment only under harsh, nonphysiological conditions.

Other suitable nitric oxide/nucleophile complexes include those having the following formulas:

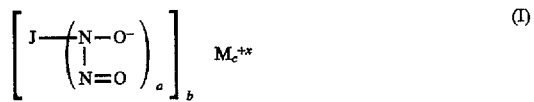

wherein J is an organic or inorganic moiety, preferably a moiety which is not linked to the nitrogen of the $N_2O_2^-$ group through a carbon atom, $M^{+x}$ is a pharmaceutically acceptable cation, where x is the valence of the cation, a is 1 or 2, and b and c are the smallest integers that result in a neutral compound, preferably such that the compound is not a salt of alanosine or dopastin, as described in U.S. Pat. No. 5,212,204 and incorporated herein by reference;

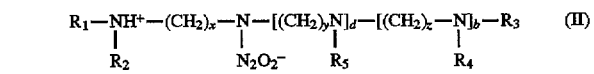

wherein b and d are the same or different and may be zero or one, $R_1$, $R_2$, $R_3$, $R_4$, and $R_5$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12, as described in U.S. Pat. No. 5,155,137 and incorporated by reference;

wherein B is

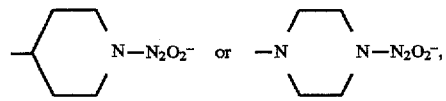

$R_6$ and $R_7$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, f is an integer from 0 to 12, with the proviso that when B is the substituted piperazine moiety

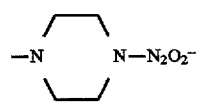

then f is an integer from 2 to 12, as described in U.S. Pat. No. 5,250,550 and incorporated by reference;

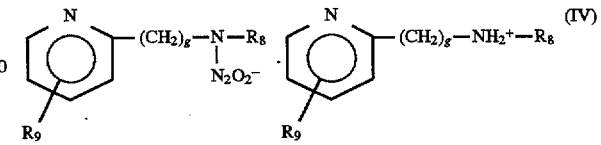

wherein $R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, $R_9$ is hydrogen or a $C_1$–$C_{12}$ straight or branched chain alkyl, and g is 2 to 6, as described in U.S. Pat. No. 5,250,550 and incorporated by reference;

(V)

wherein $R_1$ and $R_2$ are independently selected from the group consisting of a straight chain or branched chain $C_1$–$C_{12}$ alkyl group and a benzyl group, with the proviso that no branch occur on the alpha carbon atom, or else $R_1$ and $R_2$ together with the nitrogen atom they are bonded to form a heterocyclic group, preferably a pyrrolidino, piperidino, piperazino or morpholino group, $M^{+x}$ is a pharmaceutically acceptable cation, and x is the valence of the cation, as described in U.S. Pat. No. 5,039,705 and incorporated by reference;

$$K[(M)_x{}^{x'}(L)_y(R^1R^2N-N_2O_2)_z]$$ (VI)

wherein M is a pharmaceutically acceptable metal, or, where x is at least two, a mixture of two different pharmaceutically acceptable metals, L is a ligand different from ($R^1R^2N-N_2O_2$) and is bound to at least one metal, $R^1$ and $R^2$ are each organic moieties and may be the same or different (with the proviso that where M is copper, x is one, L is methanol, and y is one, that at least one of $R^1$ or $R^2$ is not ethyl), x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary, as described in U.S. Pat. No. 5,389,675 and incorporated by reference; and $$[R-N(H)N(NO)O-]_yX$$ (VII)

wherein R is $C_{2-8}$ lower alkyl, phenyl, benzyl, or $C_{3-8}$ cycloalkyl, any of which R groups may be substituted by one to three substituents, which are the same or different, selected from the group consisting of halo, hydroxy, $C_{1-8}$ alkoxy, —$NH_2$, —$C(O)NH_2$, —$CH(O)$, —$C(O)OH$, and —$NO_2$, X is a pharmaceutically acceptable cation, a pharmaceutically acceptable metal center, or a pharmaceutically acceptable organic group selected from the group consisting of $C_{1-8}$ lower alkyl, —$C(O)CH_3$, and —$C(O)NH_2$, and y is one to three, consistent with the valence of X, as described in U.S. Pat. No. 4,954,526 and incorporated by reference;

(VIII)

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$ together with the nitrogen atom to which they are bonded form a heterocyclic group, preferably a pyrrolidino, piperidino, piperazino or morpholino group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula —$(CH_2)_n$—$ON$=$N(O)NR_1R_2$, wherein n is an integer of 2–8, and $R_1$ and $R_2$ are as defined above; with the proviso that $R_1$, $R_2$ and $R_3$ do not contain a halo or a hydroxy substituent α to a heteroatom, as described in U.S. Pat. No. 5,366,997.

In accordance with the invention, the polymer is a polyether. Preferably the polyether is a polysaccharide. Polysaccharides include cellulose, starch, dextran, and xylans. The polysaccharides may be modified or derivatized. By way of illustration and not in limitation, suitable modified polysaccharides include hydroxyethylcellulose, carboxymethyl cellulose, hydroxyethyl starch, dextran ethers, dextran esters, dextran carbamates and the like.

The physical and structural characteristics of the polymers suitable for use in the present invention are not narrowly critical, but rather will depend on the end use application. It will be appreciated by those skilled in the art that where the polymer-bound nitric oxide/nucleophile adduct compositions of the present invention are intended for topical, dermal, percutaneous, or similar use, they need not be biodegradable. For some uses, such as ingestion or the like, it may be desirable that the polymer of the polymer-bound compositions slowly dissolves in a physiological environment or that it is biodegradable.

The polymer-bound nitric oxide releasing compositions of the present invention will find utility in a wide variety of applications and in a wide variety of forms depending on the biological disorder to be treated. For example, the polymer may itself be structurally sufficient to serve as an implant, patch, stent or the like. Further, by way of illustration, the polymer-bound composition may be incorporated into other polymer matrices, substrates or the like, or it may be microencapsulated, or the like.

The nitric oxide-releasing complexes having $N_2O_2^-$ functional groups, including the compounds described above, may be bound to the polymer support in a number of different ways. For example, the compounds described above may be bound to the polymer by coprecipitation of such compounds with the polymer. Coprecipitation involves, for example, solubilizing both the polymer and the nitric oxide/nucleophile compound and evaporating the solvent.

Alternatively, nitric oxide-releasing $N_2O_2^-$ functional groups may be bound to the polymer by formation of a nitric oxide/nucleophile complex of the types and having the formulas of those described above, in situ on the polymer. The $N_2O_2^-$ functional group may be attached to an atom in the backbone of the polymer, or it may be attached to a group pendant to the polymer backbone, or it may simply be entrapped in the polymer matrix. Where the $N_2O_2^-$ functional group is in the polymer backbone, the polymer includes in its backbone sites which are capable of reacting with nitric oxide to bind the nitric oxide for future release. For example, where the polymer is polyethylenimine, the polymer includes nucleophilic nitrogen atoms which react with nitric oxide to form the $N_2O_2^-$ functional group at the nitrogen in the backbone. Where the $N_2O_2^-$ functional group is a group pendant to the polymer backbone, the polymer contains, or is derivatized with, a suitable nucleophilic residue capable of reacting with nitric oxide to form the $N_2O_2^-$ functionality. Reaction of the polymer which contains a suitable nucleophilic residue, or of the suitably derivatized polymers with nitric oxide thus provides a polymer-bound nitric oxide-releasing $N_2O_2^-$ functional group.

The polymer-bound nitric oxide/nucleophile compositions of the present invention have a wide range of biological utility. In view of the growing awareness that nitric oxide is an especially versatile and important bioeffective species, having been implicated mechanistically in such critical bodily functions as vasorelaxation, neurotransmission and the immunological response (Moncada et al., Pharmacol. Rev. 43, 109–142, 1991), the compositions of the present invention find utility in applications where nitric oxide release is needed. For example, the polymer-bound nitric oxide releasing $N_2O_2^-$ functional groups may be bound to the surface of a vascular graft to reduce its thrombogenicity.

The following are further illustrative of, and not in any way in limitation of, the broad uses and applications of the polymer-bound compositions of this invention. Thus, for example, in view of dramatic but short-lived pulmonary vaso- and bronchodilatory properties exhibited by nitric oxide (Roberts et al., Circulation (Suppl. II) 84:A1279, 1991), administration of polymer-bound nitric oxide/nucleophile adduct compositions into the lungs in aerosolized form may be used in treating a variety of pulmonary disorders. Oral dosage forms for long-lived drugs containing anionic $N_2O_2^-$ functional groups that survive the acid conditions of the stomach may be used for the treatment of hypertension. Since natural, endogenous nitric oxide has been identified as an effector of penile erection (Blakeslee, New York Times, Jan. 9, 1992, page A1), the polymer-bound nitric oxide/nucleophile adduct compositions of the present invention may be incorporated into suitable penile implants, dermal patches or condoms for treatment of impotence in men. The ability of certain monomeric nitric oxide/nucleophile adducts to inhibit platelet aggregation coupled with their demonstrated cytostatic activity allows for an invaluable two-pronged approach to prevention of restenosis following angioplasty; stents fabricated with polymer-bound nitric oxide-releasing $N_2O_2^-$ functional group compositions may be used both to inhibit cell division in areas with damaged endothelium and to prevent adhesion of platelets at these locations as well, minimizing the risk of recurring blockage. With an inverse relationship between generation of nitric oxide by tumor cells and their metastatic potential having been proposed (Radomski et al., Cancer Res. 51, 6073–6078, 1991), polymer-bound nitric oxide/nucleophile compositions may be used to reduce the risk of metastasis in cancer patients. Similarly, it is contemplated that the polymer-bound nitric oxide/nucleophile adduct compositions of the present invention may be used to coat prostheses and medical implants, such as breast implants, prior to surgical connection to the body as a means of reducing the risk of solid state carcinogenisis associated therewith. With nitric oxide being additionally implicated in gastric motility, neurotransmission, nociception, and other natural roles, the compositions of this invention may be used for those applications as well.

One skilled in the art will appreciate that suitable methods of administering the polymer-bound nitric oxide-releasing $N_2O_2^-$ functional group compositions of the present invention to an animal are available, and, although more than one route can be used to administer a particular composition, a particular route can provide a more immediate and more effective reaction than another route. Pharmaceutically acceptable carriers are also well-known to those who are skilled in the art. The choice of carrier will be determined in part by the particular composition, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the polymer-bound composition dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The polymer-bound nitric oxide-releasing compositions of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immedlately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compositions employed and the condition of the animal, as well as the body weight of the animal to be treated. The size of the dose also will be determined by the existence, nature, and extent of any adverse side-effects that might accompany the administration of a particular composition.

The following examples further illustrate the present invention, but do not limit the scope thereof.

EXAMPLE I

This example illustrates the preparation of a polysaccharide polymer containing pendant $[N_2O_2]$ groups by two different methods.

A. Dextran (MW=515,000, 9 g, 55 mmole, 167 meq-OH, available from Sigma Chemical Co., St. Louis, Mo.) was dissolved in 800 ml water. Sodium hydroxide (8 ml, 10M, 80 mmole) and cyanogen bromide (CNBr, 8 g, 75 mmole), freshly dissolved in 100 ml water, were added to the dextran solution. Diethylenetriamine (DETA, 24.7 g, 222.9 mmole) or dipropylenetriamine (DPTA, 31.8 g, 222.9 mmole) was added quickly to the activated dextran solution. The pH was adjusted to 10.0 and the solution was continuously stirred overnight. The next day, the solution was extracted with two 150-ml volumes of methylene chloride and dialyzed overnight against cold running water. After adjusting the pH of the solution to 7.0, the solution was freeze-dried to yield a white solid, which was crushed to a powder (9.6 g for DETA-grafted dextran and 9.2 g for DPTA-grafted dextran). The success of the grafting was ensured by a titration of the grafted dextran (DETA-dextran) against 1N NaOH.

The DPTA- or DETA-grafted dextran (3.6 g) was crosslinked by dissolution in 15.6 ml of water and 2 ml of 10M NaOH, pouring the resulting solution into 300 ml of light mineral oil in a Waring blender, stirring for two minutes and adding CNBr (2 g, 18.87 mmole), freshly dissolved in water (16 ml), to the suspension, and stirring for an additional two minutes followed by extraction of the suspension with petroleum ether (300 ml, 3×), ethanol (95%, 500 ml, 2×) and absolute ethanol (500 ml).

The resulting DETA-grafted microspheres (1 g) were suspended in dry tetrahydrofuran (THF, 25 ml) and stirred under NO pressure (70 psi) for 48 hrs. At the end of this period, the microspheres were filtered, washed with 200 ml THF, and dried. DPTA-grafted microspheres (0.6 g) were likewise suspended in acetonitrile (25 ml), reacted with NO and worked up under similar conditions. Approximately 40 nmoles NO per mg in 1N HCl were obtained from DETA-grafted microspheres. Approximately 650 nmoles NO per mg in 1N HCl were obtained from DPTA-grafted microspheres.

B. The NO adduct of DPTA ("DPTA-NONO," [$H_2N(CH_2)_3]_2N[N(O)NO]H$, zwitterionic form) was prepared as described by Hrabie et al., *J. Org. Chem.*, 58, 1472–1476 (1993). Dextran (3.6 g, 22.2 mmole) was dissolved in 15.6 ml water. Sodium hydroxide (5 ml, 10M, 50 mmole) and DPTA-NONO (1.5 g, 9.2 mmole) were added to the solution. The solution was then poured into light mineral oil (300 ml) in a Waring blender and the mixture was stirred for 2 min. CNBr (5 g), freshly dissolved in 35 ml water, was added and the stirring was continued for another 2 min. The solution was worked up in petroleum ether (300 ml, 3×), 95% ethanol (500 ml), and 35% ethanol (1 liter, 3×). The absorbance of the last wash at 262 nm was determined. When no peak corresponding to the DPTA-NONO was observed, the microspheres were finally dehydrated by washing with 1 liter of absolute ethanol. The filtered and dried product weighed 2.7 g. Microspheres were obtained using a CNBr:dextran-OH molar ratio of 0.70 (3.6 g dextran crosslinked with 5 g CNBr and 5 ml 10M NaOH).

These NONOate grafted microspheres, i.e., those containing the [N(O)NO]$^-$ functional group, were analyzed for NO content. The in vitro NO release profiles were determined using a nitric oxide analyzer (Lear-Siegler Corp., Englewood, Colo.). The sampling chamber consisted of a gas impinger (bubbler) bottle modified at both ends with a two-way valve that allowed NO gas to accumulate in the chamber. One end of the sampling chamber was connected to the NO analyzer while the other end was connected to a flow meter and a helium gas tank. Helium gas was pumped through the system at 10 psig and the flow meter was adjusted to 150–200 ml/min. The sampling chamber was charged with 50 ml of 1M HCl or other appropriate medium and the solution was degassed. Weighed quantities of the NONOate-grafted microspheres were added to the aqueous solution (pH=7.0, phosphate buffered saline or 1N HCl, 50 ml) contained in the headspace analyzer. The nitric oxide that accumulated in the headspace of the suspension was swept with helium into the NO analyzer. The NO release studies were performed either entirely at ambient temperatures or initiated at ambient temperatures following which the sample suspension was heated in steps of 10° C. Following this period, nitric oxide was collected for various periods in the headspace, and then swept into the analyzer for a period of 2 min. The resulting signals were integrated by a Hewlett-Packard 350 integrator.

Standard curves for NO were prepared by injecting various volumes of potassium nitrate (100 or 1000 µM) into a hot solution of vanadium(III) chloride (1M in 1N HCl). The resulting NO was similarly swept into the NO analyzer. The peak areas from the generated NO were plotted against the corresponding nanomoles of nitrate, with the assumption that nitrate was quantitatively reacted to form NO in the vanadium chloride-reducing medium. Approximately 190 nmoles of NO were obtained per mg of the microspheres produced from DPTA-NONO.

EXAMPLE II

This example illustrates the preparation of polyethyleneimine cellulose NONOates.

Polyethyleneimine cellulose (PEI Cellulose) (7.0 g, 15.4 mmol) with 70 ml acetonitrile was placed in a modified Ace thread reaction bottle equipped with a magnetic stir bar. The solution was charged with nitrogen gas for 10 minutes through a 4-way gas valve setup that consisted of two gas inlets for NO and N$_2$ that could be delivered simultaneously; a third outlet was used to keep the system open. All gas connections were made with transparent Teflon tubes and stainless steel swagelock fittings. Nitric oxide gas was then administered at a pressure of 70 psig for 30 minutes and the reaction bottle was closed, keeping the reaction under pressure. This procedure for administering NO gas was repeated every other day for 10 days after which the excess NO was vented and N$_2$ gas was administered for 15 minutes. The yellow product (6.82 g) was isolated by filtration, washed with acetonitrile and then with ether, and dried in vacuo overnight. The polyethyleneimine cellulose polymer released approximately 67 nmoles of NO/mg of polymer in a pH 7.4 buffer.

EXAMPLE III

This Example illustrates the synthesis of polyethyleneimine cellulose (PEI Cellulose) NONOate fibers.

Epichlorohydrin (0.43 mL) and triethylamine (1.0 mL) were added to cellulose fibers (2.0 g) in 100 mL of distilled water. This solution was shaken for 24 hours at room temperature, filtered and then washed with distilled water to remove unreacted starting material. The fibers were resuspended in 100 mL distilled water and 3.0 g of polyethyleneimine (PEI, MW 600) was added. The PEI-grafted fibers were then filtered, washed with distilled water and dried at room temperature for 24 hours. High pressure (70 psig) nitric oxide gas was used to derivatize the fibers for 24 hours. The product was isolated by filtration, washed with 200 mL acetonitrile and then with 100 mL ether and dried overnight at room temperature. The PEI Cellulose NONOate fibers were found to release 0.98 nmoles of NO/mg of polymer in phosphate buffered saline at pH 7.2.

All publications cited herein are hereby incorporated by reference to the same extent as if each publication were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A polymeric composition capable of releasing nitric oxide, said composition comprising a polysaccharide including a nitric oxide-releasing [$N_2O_2$] functional group selected from the group consisting of X–[N(O)NO] and [N(O)NO—]X, wherein X is an amine-group-containing moiety bonded to said –[N(O)NO] or [N(O)NO–] and wherein the [$N_2O_2$] group is bonded in said polysaccharide through said moiety X.

2. A polymeric composition capable of releasing nitric oxide, said composition comprising a coprecipitation product of a polysaccharide and a compound comprising a nitric oxide-releasing [$N_2O_2$] functional group selected from the group consisting of X–[N(O)NO] and [N(O)NO–]X, wherein X is an amine-group containing a moiety bonded to said –[N(O)NO] or [N(O)NO–].

3. The polymeric composition of claim 1, wherein said nitric oxide-releasing [$N_2O_2$] functional group is included in said polysaccharide from a compound of the formula:

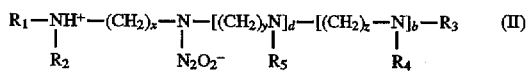 (II)

wherein b and d are the same or different and may be zero or one, $R_1$, $R_2$, $R_3$, $R_4$, and $R_5$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12.

4. The polymeric composition of claim 2, wherein said nitric oxide-releasing [$N_2O_2$] functional group is from a compound of the formula:

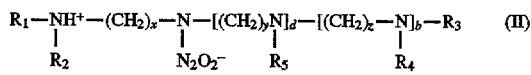 (II)

wherein b and d are the same or different and may be zero or one, $R_1$, $R_2$, $R_3$, $R_4$, and $R_5$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12.

* * * * *